United States Patent
Gosalvez Berenguer et al.

(10) Patent No.: US 7,993,827 B2
(45) Date of Patent: Aug. 9, 2011

(54) PROCEDURE FOR THE DETERMINATION OF FRAGMENTATION OF DNA IN ANIMAL SPERM

(75) Inventors: Jaime Gosalvez Berenguer, Madrid (ES); Jose Luis Fernandez Garcia, La Coruña (ES); Vicente Goyanes Villaescusa, La Coruña (ES)

(73) Assignee: Universidad Autonoma de Madrid, Madrid (ES)

( * ) Notice: Subject to any disclaimer, the term of this patent is extended or adjusted under 35 U.S.C. 154(b) by 248 days.

(21) Appl. No.: 10/586,298

(22) PCT Filed: Jan. 26, 2005

(86) PCT No.: PCT/IB2005/000187
§ 371 (c)(1),
(2), (4) Date: Apr. 17, 2007

(87) PCT Pub. No.: WO2006/079864
PCT Pub. Date: Aug. 3, 2006

(65) Prior Publication Data
US 2007/0281298 A1    Dec. 6, 2007

(30) Foreign Application Priority Data

Jan. 26, 2004   (ES) .................................. 200400163

(51) Int. Cl.
*C12Q 1/68* (2006.01)
*C07H 21/02* (2006.01)
(52) U.S. Cl. .......................................... 435/6; 536/22.1
(58) Field of Classification Search ...... 435/6; 536/23.1
See application file for complete search history.

(56) References Cited

OTHER PUBLICATIONS

Donnelly et al., "Differences in nuclear DNA fragmentation and mitochondrial integrity of semen and prepared human spermatozoa," Human Reproduction, 2000, vol. 15, No. 7, pp. 1552-1561.*
Fernandez et al., "DNA breakage detection-FISH (DBD-FISH) in human spermatozoa: technical variants evidence different structural features," Mutation Research, 2000, vol. 453, pp. 77-82.*
Revel et al., "Resveratrol, a natural aryl hydrocarbon receptor antagonist, protects sperm from DNA damage and apoptosis caused by benzo(a)pyrene," Reproductive Toxicology, 2001, vol. 15, pp. 479-486.*
Fernandez et al., "The Sperm Chromatin Dispersion Test: A Simple Method for the Determination of Sperm DNA Fragmentation," J. Androl, Jan./Feb. 2003, vol. 24, No. 1, pp. 59-66.*
Richthoff et al., "The impact of testicular and accessory sex gland function on sperm chromatin integrity as assessed by the sperm chromatin structure assay (SCSA)," Human Reproduction, 2002, vol. 17, No. 12, pp. 3162-3169.*
Donnelly et al., "The effect of ascorbate and a-tocopherol supplementation in vitro of DNA integrity and hydrogen peroxide-induced DNA damage in human spermatozoa," Mutagenesis, 1999, vol. 14, No. 5, pp. 505-511.*
Donnelly et al., "Assessment of DNA integrity and morphology of ejaculated spermatozoa from fertile and infertile men before and after cryopreservation," Human Reproduction, 2001, vol. 16, No. 6, pp. 1191-1199.*
Irvine et al., "DNA Integrity in Human Spermatozoa: Relationships with Semen Quality," J. Andrology, 2000, vol. 21, No. 1, pp. 33-44.*
Sakkas et al., "Nature of DNA Damage in Ejaculated Human Spermatozoa and the Possible Involvement of Apoptosis," Biol. of Reprod., 2002, vol. 66, pp. 1061-1067.*
Agarwal et al., "Sperm Chromatin Assessment," Textbook of Assisted Reproductive Techniques, 2nd Edition, Editors: Gardner et al., Taylor & Francis Group, plc, London, UK, 2004, Chapter 7, pp. 93-106.*
Coils et al., "Sequential G-banding FISH on human sperm chromosomes," Chromosome Research, 1997, vol. 5, pp. 457-461.*
Kruger et al., "New Method of Evaluating Sperm Morphology with Predictive Value for Human In Vitro Fertilization," Urology, 1987, vol. 30, No. 3, pp. 248-251.*
Connell, Mo et al. Differences in mitochondrial and nuclear DNA status of high-density and low-density sperm fractions after density centrifugation preparation. Fertility and Sterility, vol. 79, suppl. 1, Mar. 2003.*
Spano, M et al. Nuclear chromatin variations in human spermatozoa undergoing swim-up and cryopreservation evaluated by the flow cytometric sperm chromatin structure assay. Molecular Human Reproduction, vol. 5, No. 1, pp. 29-37, 1999.*
Januskauskas, A. et al. Assessment of sperm quality through fluoremetry and sperm chromatin structure assay in relation to field fertility og frozen-thawed semen from swedish AI bulls. Theriogenology, vol. 55: pp. 947-961, 2001.*
Fernandez, J.L. et al. The sperm chromatin dispersion test: a simple method for the determination of sperm DNA fragmentstion. J. Andrology, vol. 24, No. 1, pp. 59-66, 2003.*
Bezanehtak, H. et al. Study of demembranated, reactivated human spermatozoa with decondensed nuclei. J. Exp. Zool., vol. 284(7), pp. 789-797, 1999.*
Richthoff, J. et al. The impact of testicular and accessory sex gland function on sperm chromatin integrity as assessed by the sperm chromatin structure assay (SCSA). Human Reproduction, vol. 17, No. 12, pp. 3162-3169, 2002.*

* cited by examiner

*Primary Examiner* — Prabha Chunduru
(74) *Attorney, Agent, or Firm* — Ladas & Parry LLP

(57) ABSTRACT

The present invention describes a method for the determination of DNA fragmentation in animal sperm. It particularly refers to a procedure to evaluate the integrity of the chromatin/DNA of the sperm by means of a treatment of the sample with a denaturing solution followed, optionally by a stain; a subsequent treatment with a lysis solution that does not contain a protein denaturing detergent, followed, optionally, by a stain; and an evaluation of the integrity of the chromatin/DNA. The present invention also refers to a Kit to evaluate the quality of the sperm of animals which includes a DNA denaturing solution and a lysis solution that does not contain a protein denaturing detergent.

12 Claims, 5 Drawing Sheets

Figure 1. Sperm cells treated with one solution (lysis +denaturation)

Figure 2. Sperm cells treated with two sequential solutions (1$^{st}$ lysis +2$^{nd}$ denaturation)

PROCEDURE FOR THE DETERMINATION OF FRAGMENTATION OF DNA IN ANIMAL SPERM

FIELD OF THE INVENTION

This invention has its field of application within the health sector, principally that related to biological reproduction, in particular it is directed to procedures and methods for the determination of the quality of semen in animals.

BACKGROUND OF THE INVENTION

Currently 6% of males, of fertile age, in western countries have some kind of disease which prevents normal reproduction. To this effect, the World Health Organisation (WHO) has put together a series of laboratory procedures in a single protocol which standardises the analysis of the quality of semen in the international setting. These studies are centred on the determination of the concentration, morphology and motility of the sperm, complemented with the evaluation of certain functional tests, as well as determined biochemical and enzymatic parameters of the semen (WHO, 1999). This group of tests can estimate the total volume of the same and the concentration of sperm per milliliter and it can be diagnosed whether the infertility of the male is due to an absence (azoospermia) or a clear decrease (oligospermia) by the quantity of sperm in the ejaculate. Also, it determines the possible existence of motility problems (asthenozoospermia) which makes it impossible for these cells to cross the uterine cavity and successfully reach the outer third of the Fallopian tubes. It is also analysed whether there are serious morphology problems of their components (head, neck, tail) (teratozoospermia), given that these variations have repercussions in the capacity for an efficient fertilisation of the female ovule. Additionally, it likewise explores the participation of the glands such as the prostate and seminal vesicles (infections, agenesis). Lastly, with functional tests such as the HOS test (ionic permeability of the cell membrane) or the progression capacity of the sperm in vitro, they give an idea of the fertility capacity of the semen. Finally, these laboratory studies occasionally have to be complemented with hormone profiles, testicle biopsy and/or the determination of the karyotype (chromosome study which defines the hereditary condition of the male or female sex of an individual) and/or molecular genetic tests.

Despite clinical and laboratory studies, the cause of the infertility cannot be determined in about 30%-50% of infertile males, being called idiopathic infertility. Recently, it has been recognised that damage of the sperm DNA could explain a high percentage of these cases (Evenson et al., 1999; Larson et al., 2000), in such a way that the study of DNA fragmentation of sperm is a subject of active research with continuous publications in specialised journals (Evenson et al., 2002). Chromatin anomalies, or even damage in the nuclear DNA of the sperm, could take place or even be the result of anomalies in the DNA packaging which takes place during spermatogenesis (Sailer et al., 1995). There is also even the possibility that they may be the result of damage produced by free radicals which cause oxidative stress (Aitken et al., 1998), a consequence of a possible apoptosis process (Gorczyca et al., 1993).

There are different methods for evaluating the integrity of the chromatin/DNA of human sperm. Among them is highlighted the rupture of DNA in situ by introducing labelled nucleotides in the same using enzymes such as terminal transferase (TUNEL) or DNA polymerase (in situ nick translation ISNT) (Gorczyca et al., 1993). These methods are based on the use of enzymes on the sperm fixed on slides. For that reason their efficiency is not very high, only those labelled breakages being accessible to the enzyme, which leads to a relatively low reproducibility of the results. The reagents are also expensive, therefore the techniques are only used in research, not being possible to use them for the clinical evaluation of semen. Another technique is the comet assay (Hughes et al., 1996). The sperm are included in an agarose microgel on a slide and are subjected to lysis solutions to extract the membranes and proteins. Thus, nucleoids are obtained, that is, deproteinised nuclei, in which the DNA loops have been unwound due to stretching. The nucleoids are subjected to electrophoresis in a tank filled with buffer, in such a way the DNA strands migrate to the anode, creating the image of a comet, with a head and a tail in the direction of the electrophoretic migration. These comets are stained with a fluorescent stain, to be observed under a fluorescence microscope. If the nucleus has DNA fragmentation, a large quantity of them will have migrated, and concentrated in the tail of the comet. It is a fairly sensitive test, but also relatively expensive and complicated for a conventional clinical laboratory. In fact, it requires particularly uncommon equipment: electrophoresis power source and tank, fluorescence microscope, and an image capturing system and the analysis of the same. For all these reasons it is not applicable to the clinical study of semen either and is only used for research purposes.

The current reference technique for the study of DNA fragmentation of sperm is the chromatin structure assay by Evenson (SCSA: Sperm Chromatin Structure Assay; Evenson et al., 1980; 2000; Evenson and Jost, 1994). In this technique, the sperm in suspension are added to an acid denaturing solution. Those sperm without breakages in their DNA are resistant to this acid denaturing, remaining as double strand DNA. However, the sperm with fragmented DNA themselves denature their DNA, being transformed into single chain DNA. They are then stained with acridine orange. This stain emits a green fluorescence when it binds with double stranded DNA. However, in the sperm with denatured DNA, in a single strand, this fluorochrome emits a red fluorescence. The sperm with denatured DNA are quantified using flow cytometry, to discriminate between both types of fluorescence. The SCSA is a technique with wide clinical scope, having been evaluated in a large number of patients. Using this system, it has been established that when an individual has 30% or more of the sperm with fragmented DNA, their probability of a pregnancy going to term is less than 1%, and this applies in natural fertilisation as well assisted production (Evenson et al., 1999; Larson et al., 2000).

The percentage of sperm with fragmented DNA can be more or less constant in the different spermatogenesis cycles of an individual, but can also vary due to exogenous factors, or, for example, after an intense febrile episode, such as influenza (Evenson et al., 2000). In this way, serial studies can be made, selecting those samples with a lower level of fragmentation, to subsequently be used in assisted production techniques. It is important to take into account that freezing the semen samples in liquid nitrogen does not alter the levels of DNA fragmentation, therefore this test can be done on frozen samples, which can later be used in insemination, IVF (in vitro fertilisation) or ICSI (Intracytoplasmatic Sperm Injection). This has a great operational advantage for the patient and the laboratory.

The SCSA technique, although robust and highly reproducible, is an expensive system, difficult to implement, and not very accessible to the routine laboratory (De Jonge, 2002). For this reason, the quality of the sperm DNA still cannot be evaluated routinely, despite its verified clinical value in the study of infertility.

Recently, our research group preliminarily described a technique which enabled the chromatin of human sperm to be dispersed in situ, demonstrating that those sperm incapable of dispersing the chromatin contained fragmented DNA (Fernandez, J. L. et al., *Journal of Andrology*, 2003, vol. 24, No. 1, pp. 59-66; "The Sperm Chromatin Dispersion Test: a simple method for the determination of sperm DNA fragmentation"). Using this method, samples of semen are treated sequentially in agarose microgel with an acid denaturing solution, with two lysis solutions and with a wash so that they may be dried and stained afterwards. This technique, which is called Sperm Chromatin Dispersion (SCD) test, uses excessively aggressive reagents and conditions. The described method does not give consistent results which makes repeated evaluations difficult. On the other hand, the quality and contrast of the images obtained and the reproducibility of the results are not good enough to be able to be applied commercially. Also, the structure of the sperm is affected and the tail is not visible in the samples. This problem is important, since the sperm cannot be easily distinguished from other cells in the sample, with the subsequent error in quantifying the number of sperm with damaged chromatin/DNA.

Therefore there is still the need of a reliable process which could be used routinely and easily for the study of the quality of semen in animals and in particular to evaluate the integrity of the chromatin/DNA. The process has to be robust, easy to implement, cheap and accessible to the basic laboratory. It has to resolve the previously mentioned problems. It also has to give homogenous results between laboratories and be suitable for automation.

OBJECT OF THE INVENTION

The object of the invention is a method which is rapid and precise for evaluating the integrity of the chromatin/DNA of sperm cells in animals and can be incorporated into the routine activity of any analytical, veterinary or specific for human reproduction, laboratory.

Therefore an object of the invention is a method to evaluate the integrity of the chromatin/DNA of the sperm of an animal that comprises of:

a) a treatment step of the sample containing the sperm, with a DNA denaturing solution, b) a single treatment step with a lysis solution to extract nuclear proteins, c) a step to evaluate the integrity of the chromatin/DNA of the sperm, characterised in that the lysis solution does not contain a protein denaturing detergent and essentially the tail of the sperm is not destroyed.

In general it is preferred that step a) precedes b).

As is indicated the selection of the lysis solution is critical to achieve the objectives of the invention. Among the protein denaturing detergents which must not be used we have the anionic and cationic detergents, for example SDS, sodium dodecyl sulphate, alkyl benzene sulphonate, glycolic acid hydrated salt, etc. They are detergents which greatly disrupt the membranes, with a lysis effect and at the same time are active in the denaturing of the proteins. They are used in denaturing electrophoresis where the proteins are subjected to migration assuring the complete denaturing (loss of three-dimensional structure). They are especially active at an acid pH, preferably on Gram-positive bacteria. Their activity within the detergents is high.

In the method of the invention preferably a non-ionic non protein denaturing detergent is used, that is to say a detergent which solubilises the proteins but does not denature them. Among those is preferred, toctylphenoxypolyethoxyethanol (Triton X-100), N, N-bis (3-D-Gluconamidopropyl) cholamide (bigCHAP), Brij(r) 35 P, N-decanoyl-N-methylglucamine, digitonin, dodecanoyl-N-methylglucamide, heptanoyl-N-methylglucamide, branched octylphenoxy poly (ethyleneoxy) ethanol (Igepal CA-630), N-Nonanoyl-N-methylglucamine, Nonidet P 40, N-Octanoyl-N-methylglucamine, Span 20 solution, Polysorbate 20 (Tween 20). Triton X-100 is particularly preferred due to the good results that it gives and its easy availability.

It is preferred that the lysis solution has a sufficient ionic strength to facilitate the lysis process without denaturing. We have verified that an effective solution is one which contains between 1M and 3M sodium chloride, dithiothreitol (DTT) between 0.001M and 2 M, 2-amino-2 (hydroxymethyl)-1,3 propanediol (Tris) between 0.001M and 2 M and Triton X-100 between 0.1% and 3%. Particularly suitable is a solution which contains NaCl of around 2.5M, DTT around 0.2M, Tris around 0.2M, Triton X-100 around 1% and a pH of around 7.5.

The denaturing solution of DNA is preferably acid, for example of an acid selected from the hydrochloric, acetic, nitric acid group or mixtures of these. Preferably it is a hydrochloric acid solution.

The method according to the invention has an evaluation of the integrity of the chromatin/DNA of the sperm step after steps a) and b). Although there are several alternatives for this evaluation, it is preferred that it is visual. With this aim the procedure preferably includes a sample staining step after steps a) and b). A stain which gives excellent results and allows the tail of the sperm to be visualised as well as the characteristic halo formed is a solution similar to that of Wright.

In a preferred variation the sperm are included in a medium similar to a suspension, preferably in a microgel, especially in an agarose microgel.

The invention is also directed towards a Kit to evaluate the quality of animal sperm which comprises of:

a) a DNA denaturing solution, b) a lysis solution to extract the nuclear proteins, characterised in that the lysis solution does not contain a protein denaturing detergent and essentially does not destroy the tails of the sperm. The Kit allows the carrying out of the procedure according to the invention that has just been described.

DETAILED DESCRIPTION OF THE INVENTION

Figure 1:
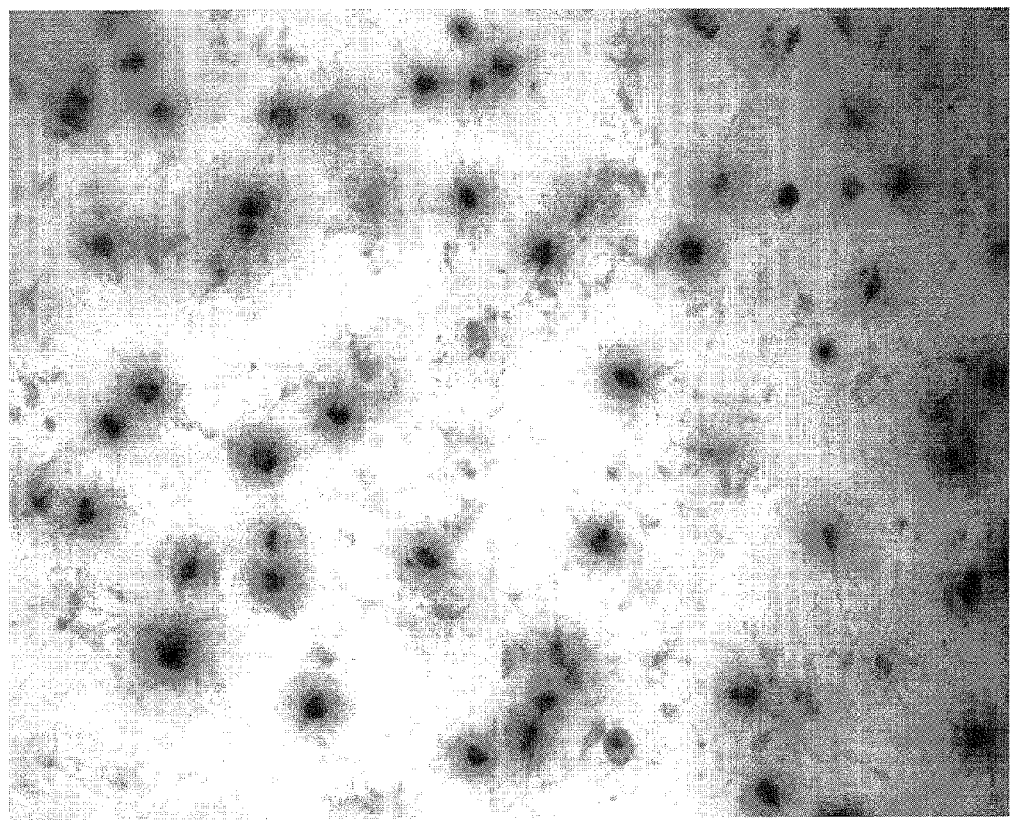
FIG. 1. Parameters used for the definition of the size of the halos in human sperm, according to the methodology of the invention. 1a: The nucleoid, which corresponds to the extensively deproteinised nucleus of the sperm, which consists of two parts: the silhouette of the sperm nucleus, called the core, in a central position, and the peripheral halo of the chromatin/DNA dispersion. The tail of the sperm is visible. 1b: A relief filter for a better visualisation and establishing of the limits between the hale and the core. 1c: Smaller diameter of the core (a) and thickness of the halo (b), as a sample of the measurements used to establish the different sizes of the halos, as is explained in the methodology of the invention.

As will be detailed, the procedure and the Kit of the invention are a simple and reliable system for the determination of the frequency of sperm with fragmented DNA. The methodology is applicable in andrology laboratories and assisted reproduction clinics and animal breeding laboratories. It also a very versatile system since it is possible to freeze the samples and analyse them when needed, without causing changes in the results of the analysis.

The procedure of the invention, which enables the evaluation of the integrity of the chromatin/DNA and the sperm from an animal comprises of:
  a) a treatment step of the sample containing the sperm, with a DNA denaturing solution;
  b) a single treatment step with a lysis solution to extract nuclear proteins, which does not contain a protein denaturing detergent and essentially does not destroy the tails of the sperm;
  c) an evaluation step of the integrity of the chromatin/DNA of the sperm.

Besides others, the principal differences of the procedure of the invention, as regards the state of the technique and specifically regarding Fernandez, J. L. et al. *Journal of Andrology*, 2003, vol. 24, No. 1, pp. 59-66, basically lie in the field of lysis and staining. Thus, a single lysis solution is used, instead of two sequential ones. The composition is different as it does not contain SDS (anionic protein denaturing detergent) or EDTA (chelating agent). It can incorporate a relatively mild, neutral, non denaturing, detergent, such as Triton X-100.

Technically these differences lead to the preservation of the tails of the sperm. It is a crucial improvement, as their detection is an indispensable piece of data to be able to discriminate whether the images of the nucleoids actually come from the sperm or correspond to other cell types that could be present, for example, desquamated cells from the genito-urinary tract, inflammatory cells, blood, etc. This persistence is achieved using a much less aggressive lysis, as well as ruling out the use of SDS.

Also, the milder lysis achieves the unfolding of the chromatin strands, better preserving the morphology of the head, or core, and obtaining dispersion halos with a higher density of the chromatin material, resulting in them being more intensely stained. As a result, the contrast and the visualisation of the different sizes of halo are very much improved, especially when Wright's stain is used.

Another significant advantage is that the absence of a protein denaturing detergent, such as SDS, allows the sequential use of the technique described here with others that enable other cell components to be visualised. Thus, on the nucleoids obtained, according to the methodology described, methods for the immunodetection of proteins, laminin protein types and other nuclear proteins can be applied, as well as the detection of RNA associated with the nuclear matrix, as the DNA is extended, the quantity of the nuclear structure being maintained as much as possible. This is important in certain research topics into the nuclear structure of the sperm.

Another additional advantage is the use of a lower amount of reagents and, consequently, there is less economic cost. For example, DTT is particularly expensive, and the reduction of the concentration described in the examples (a quarter of that described in the article) is significant to the cost.

What is inferred for all that expressed is that the procedure to patent results in much improved and more reproducible images of nucleoids of sperm as regards the state of the technique. It is possible to discriminate whether or not the nucleoids come from mature sperm or from other cell types, and the categorising of the size of the halo is much more precise and reliable. Consequently, with the procedure to patent, the determination of the levels of DNA fragmentation of the sample is much more reliable, which means it can be used routinely and simply at a low cost. Its application is relevant in different laboratories, in the clinical setting and on human samples, as well as in veterinary laboratories for the study of animal samples. This is very important, since it a test with a possible clinical application to patients.

The sequence of steps of the treatment of the sample can be made in any order, first with a DNA denaturing solution, followed by the treatment step with a lysis solution or vice versa. But it is preferred to treat the sample before with the DNA denaturing solution and afterwards with the lysis solution, since it gives better results. In another variation (lysis followed by denaturing of the DNA) the sperm with the fragmented DNA behave in a different way. In this case, they disperse fragments of chromatin/DNA, giving rise to larger sized halos. Even a single treatment with a lysis solution can be sufficient to observe this behaviour, although the discrimination of the halo sizes is not very precise.

The procedure of the invention is set out in detail below, along with some variations and optional steps. The expert in the technique will understand that there are other ways of realisation and other possibilities providing that the fundamental aspects which are described are maintained.

The first step is the preparation of the sample. It is obtained using procedures common to this field and the concentration of sperm in the sample is determined. The concentration suitable for this analysis varies between 0.1 and 20 million cells per milliliter. If the sample is highly concentrated it is adjusted to a suitable concentration by diluting it with culture medium or with a solution of buffered phosphate/saline (PBS) or similar.

The semen sample has to placed on a support for its processing according to the procedure of the invention and to make its evaluation easier. This is preferably a glass slide which can be covered with a film of standard agarose. For this, a standard agarose solution between 0.2% and 1% is prepared in distilled water in a Coplin jar or similar. It is covered with a plastic gauze and is placed in a microwave oven. The microwave oven is set to a power between 300 W-1000 W, for example 500 W, agitating the container to improve the dissolving of the agarose, leaving it until it boils. This procedure can be carried out using a thermostatic bath. When the agarose solution turns completely transparent, it will then be prepared by placing it in vertical containers of between 10 ml and 250 ml. These recipients should be previously heated between 60° C.-100° C., for example 70° C., in a bath, to keep the agarose solution in the liquid state.

Before introducing the slides into the agarose solution, these are cleaned by rubbing with a cloth to eliminate possible impurities. The slides are submerged vertically, holding them with tweezers in the frosted area, for between 1-60 seconds, withdrawing them and returning them to be submerged between 1 and 10 times, until forming a homogenous film on the slide. These are deposited horizontally on a smooth surface, for example glass or metal, and cooled to between 1° C. and 15° C., preferably 4° C. This plate, with the slides, is place in the refrigerator at 4° C. for 30 minutes, until it is verified that the agarose has gelled on the surface of the slides. The trays are removed from the refrigerator and the surface of the slide that was in contact with the plate is cleaned with blotting paper. Next, the slides are placed horizontally into a drying chamber at a temperature range between 37° C.-100° C., until the agarose is completely dry and forms a fine film adhered to the glass. The slides thus treated can be used immediately or stored in a well sealed box at ambient (room) temperature for several months.

To make the processing of the sample that contains the sperm easier, this can be included in a medium with similar characteristics to those of a suspension such as, for example, an agarose microgel. In this case, a solution of low melting/low gelling agarose at a concentration between 0.5% and 2% in distilled water is prepared. The gelling of this agar is carried out in a microwave oven or a thermostatic bath, and is then kept between 30° C. and 37° C. in a tube placed in a thermostatic bath or drying chamber. The semen and the agarose solution are mixed carefully in an Eppendorf tube or similar, in such a way that the latter is in a concentration between 0.3% and 1%. For example, 70 microliters of agarose solution+30 microliters of the sample. It is important that the agarose solution is no higher than 37° C., so as not to damage the cells.

Finally, to get the sample over the support, the covered slides are placed on a smooth and cool surface of glass or metal, with a temperature that varies between 1° C. and 15° C., avoiding air bubbles forming. It is recommended to deposit a drop of between 5-200 microliters of the mixture with a micropipette, placing a cover slip over the drop. As a precaution, it is recommended to process each sample in duplicate, and use a control sample each time the technique is applied. The plate with the slides, is placed in a refrigerator at 4° C. for between 2 to 30 minutes until suitable gelling of the agarose is produced. Once the gelling has taken place, the slides are then withdrawn very smoothly, from the same refrigerator and making sure the microgel is not damaged.

Once the samples are suitably prepared for their easy and repeated handling, they are then treated according to the procedure of the invention with a treatment step with DNA denaturing solution and a lysis step to extract the nuclear proteins.

In a preferred variation the slides with the sample are first placed in an horizontal position in a recipient that contains the denaturing solution. The DNA denaturing solution can be acid, for example a solution of acetic acid, nitric acid, sulphuric acid, or alkaline such as for example a solution of sodium hydroxide, barium hydroxide, potassium hydroxide, in weak concentrations. In a preferred variation a solution of hydrochloric acid is used at a concentration that varies between 0.01N and 0.5N, preferably between 0.1N and 0.3N, particularly preferred is a concentration around 0.2N. It is recommended that this solution is prepared the same day as carrying out the test and keeping the slides incubating in the DNA denaturing solution between 1 and 15 minutes at a temperature between 1° C. and 37° C., preferably 18° C.-25° C., preferably 20-22° C.

Once this part of the process is finished, the lysis of the sample is then carried out with a single lysis solution which is sufficiently mild so as not to destroy the tails of the sperm. For this, each slide is submerged, in a horizontal position, in another recipient which contains it.

As mentioned earlier, the lysis solution is selected in such a way that it achieves the unfolding of the chromatin strands preserving the morphology of the head section better and therefore the formation of the characteristic halos with a higher density of chromatin material. It must also be sufficiently mild for the preservation of the tails of the sperm. This is achieved by ensuring aggressive detergents and protein denaturers are avoided. Additionally, control of the ionic concentration can also enable this effect to be modulated.

In a preferred variation this solution is composed of: sodium chloride between 1M and 3M, preferably between 2M and 3M; dithiothreitol (DTT) between 0.001M and 2M, preferably between 0.01M and 0.8M; 2-amino-2 (hydroxymethyl)-1,3-propanediol (Tris) between 0.001M and 2M, preferably between 0.01M and 0.4M; and Triton X-100 between 0.1% and 3%, preferably between 0.5%-1.5%. This solution is adjusted to a pH between 6.5 and 8.5, preferably 7-7.5.

There are other alternative lysis solutions, or the concentrations and times and incubation temperatures of the solution can be varied provided that its functional characteristics are maintained. Also, as alternatives to DTT, there are compounds like beta-mercaptoethanol and other reducing agents. As alternatives to Tris, other buffer solutions can be used, such as Hepes, Mops, and Pipes. As an alternative to Triton X-100, other neutral detergents can be used as mentioned above.

Depending on the solution employed and the type of sample, the preparations are incubated in the lysis solution for between 1 and 60 minutes, preferably between 15 and 35 minutes, a time of around 25 minutes is particularly preferred; and at a temperature between 1° C. and 37° C., preferably between 18° C.-25° C., and a temperature between 20° C.-22° C. is particularly preferred.

As a total alternative to the processes described previously, the order of incubation in the denaturing and lysis solutions can be reversed. The effects on the chromatin of the sperm also enables the sperm with damaged chromatin/DNA to be discriminated from the rest of the sperm. The details of the differences obtained will be described in Example Number 6.

After treatment with DNA denaturing solution and with the lysis solution, the preparations can be washed to eliminate the remains of these solutions. For this, the mildest possible wash solution is used, avoiding chelating agents or detergents. For example, they are submerged in the horizontal position in a recipient containing abundant distilled water or a buffer solution or physiological saline for a time between 1 and 60 minutes.

The sample is then dehydrated. For this increasing concentrations of alcohol can be used. For example, the slides are raised and submerged in a horizontal position, in recipients with a series of increasing concentrations of ethanol, between 5% and 100%, for 30 seconds to 60 minutes each one and then the preparations are left to dry in the air. As an alternative to the incubations in a series of ethanol, the preparations can be dehydrated by incubating in different alcohols such as methanol, or even left to dry in the air or in a drying chamber.

Once dry, the already processed slides containing the semen sample can be kept in storage boxes at ambient (room) temperature for months. This helps to separate the treatment process according to the invention and the next step of evaluating the integrity of the chromatin/DNA of the sperm. The storage enables repeated evaluations at different time intervals of several samples from the same individual.

Once the samples are treated according to the invention, they pass on to the evaluation step. There are several possible processes to evaluate the integrity of the chromatin/DNA of the sperm as has been indicate earlier. The advantage is that the samples treated according to the invention have a much clearer to visualise halo and the structure of the sperm has been maintained, particularly the integrity of the tails, which enables them to be clearly distinguished from other types of cells.

In a preferred variation a stain is applied to the sample which facilitates the visual evaluation. Choosing suitable staining conditions can obtain high quality images and a high consistency in the evaluation results. There are several strategies for staining, depending on whether a conventional, clear field microscope or fluorescence microscope is used.

Stain for Observing under a Clear Field Microscope:

In this case stains that can be used are, Wright, Giemsa, Orcein, Schiff reagent, Acetic Carmine, thiazine types and mixtures of Romanowsky types or derivates of the aforementioned (see Chromosome banding by A T Sumner, pp. 90-91).

Stains such as that of Wright are preferred due to the more intense staining of the sample and in particular the halos. With these stains the contrast and the visual discrimination of the different sized halos are significantly improved. They also have the advantage of low cost and easy availability for any type of laboratory. Their use enables the tails to be visualised, since these are not normally visible in DNA stains with fluorochromes used for fluorescence microscopes. It is important to emphasise that this stain is very easily handled to achieve the appropriate staining level, a fact not possible with Diff-Quik or similar ones.

Other stains, such as Diff-Quik, described by Fernandez, J. L. et al. in *Journal of Andrology*, 2003, vol 24, No. 1, pp 59-66, are considerably weaker and do not achieve adequate contrast of the halo as regards the background. Consequently, when the halo is much dispersed, it is normally difficult to visualise its peripheral outline, sometimes being mistaken for a small halo, thus assigning the fragmentation category to a sperm which contains intact DNA. That is to say, the procedure of the publication has a tendency to over-estimate the fragmentation levels, particularly in clear field staining. This is relatively awkward for a test with possible application to individuals. Therefore, it is obvious that this improvement has enormous relevance in the reliability of the technique.

In a variation of the staining of the sample, Wright's solution (Merck 1.01383.0500) is mixed with a phosphate buffer solution for example at pH 6.88 (Merck 1.07924.1000) in a ratio of 1:30 and 30:1 (v/v). A layer of stain is deposited, horizontally, which should cover the dry microgel. The staining time to achieve an optimum contrast varies between 30 seconds and 60 minutes. It is recommended to blow the stain layer occasionally. The excess stain is decanted, the slides are gently washed with running water and left to dry. If the stain is excessive, it can be washed, at the same intensity, in water. Another possibility is to de-stain in ethanol, dry and stain again. If the stain is weak, particularly in the region of the dispersion halos of the chromatin, it can be stained again directly with Wright's solution.

As alternatives, other stains can be used such as Hemacolor 2 (Merck 1.11956) and Hemacolor 3 (Merck 1.11957), Giemsa, as well as other staining solutions of the same family.

Staining for Observation under a Fluorescence Microscope:

Depending on the availability of fluorescence filters, the samples can be stained with fluorochromes specific for DNA of the DAPI type, Hoechst 33258, ethidium bromide, propidium iodide, etc., in an antifading medium (for example; Vector H-1000).

If permanent preparations are desired, the processed and stained slides can be included in mounting media (for example, Entellan; Merck 1.07961).

Finally, the integrity of the chromatin/DNA of the sperm is evaluated by proceeding to distinguish the cell types. As has already been mentioned, the procedure of the invention makes this evaluation much easier as regards the state of the technique.

The images obtained can be studied by direct visual analysis or by applying digitalised images analysis software, obtained by using analogue or digital cameras, coupled to the microscope platforms.

Initially, the study of a minimum of 500 sperm per sample is recommended, adopting the following basic criteria (see FIG. 1 and FIG. 2):

1. Sperm without chromatin dispersion halo (FIG. 1).
2. Sperm without chromatin dispersion halo and degraded: those without showing a halo, have a head fragmented into granules or show very weak staining. (FIG. 1).
3. Sperm with a small sized dispersion halo: the thickness of the halo less than or equal to ⅓ of the lower diameter of the core (FIG. 1).
b 4. Sperm with a medium sized dispersion halo: the thickness of the halo is between: more than ⅓ of the lower diameter of the core and less than the diameter of the core (FIG. 1).
5. Sperm with a large-sized dispersion halo: sperm where the halo is greater than or equal to the lower diameter of the core. (FIG. 1).
6. Others: cell nuclei which do not belong to sperm. One of the morphological characteristics which distinguish them is the absence of a tail.

Figure 2:
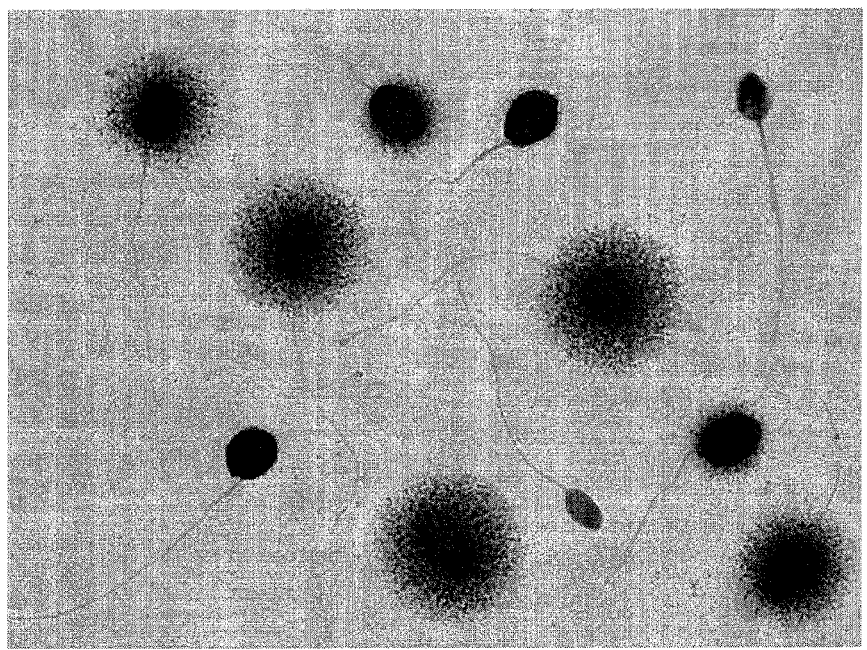
FIG. 2. Different type of sperm defined according to the size of the halo which is produced after applying the methodology of the invention. 2a: Sperm with a large size halo. 2b: Sperm with a medium sized halo. 2c: Sperm with a small sized halo. 2d: Sperm with no halo. 2e: Sperm without a halo and degraded. 2f: General field in which the different types of previously described sperm are observed.
Figure 3:
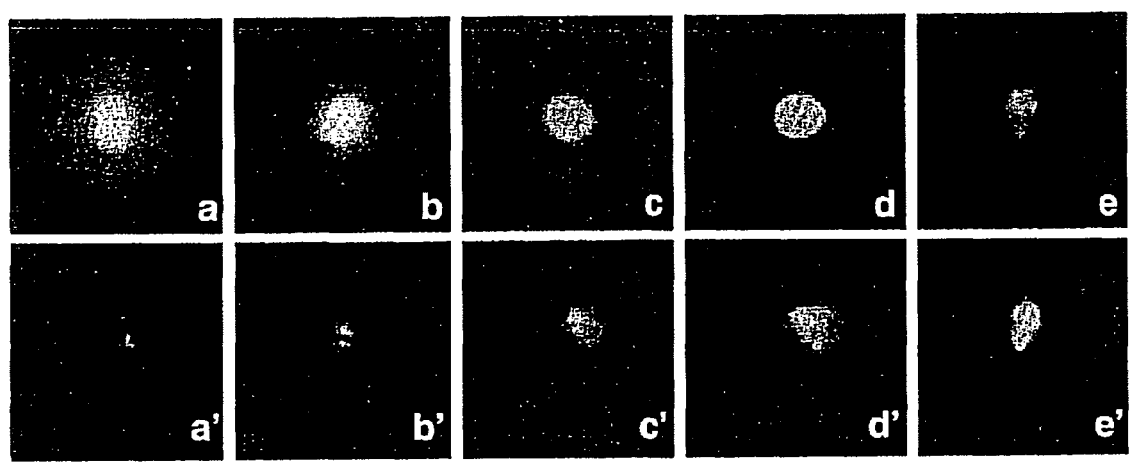
FIG. 3. Correlation between the different halo sizes visualised after staining with DAPI (a-e, fluorescein blue) and the in situ hybridisation signal using a total human genomic DNA probe, according to DBD-FISH methodology (a'-e', fluorescein red) to visualise the level of DNA fragmentation. 3a: Sperm with halo and low hybridisation signal (3a'). 3b: Sperm with medium halo and low hybridisation signal, although slightly higher than in the previous case (3b'). 3c: Sperm with a small halo and a notable increase in the level of hybridisation (3c'). 3d: Sperm without a halo and a high level of hybridisation (3d'). 3e: Degraded sperm and showing an irregular hybridisation distribution (3e').

Sperm with fragmented DNA may be considered as those without a chromatin dispersion halo 1, those that are present without chromatin dispersion halo and degraded 2, and those with a small sized dispersion halo 3. Those sperm with a medium- or large-sized chromatin dispersion halo and DNA fragmentation derive from the results obtained using the DBD-FISH technique (DNA Breakage Detection-Fluorescence In Situ Hybridization; Fernandez et al., 1998; 2000; 2002; Fernandez and Gonsálvez, 2002). This procedure enables the detection and quantification of DNA breakages cell nuclei, deproteinised and subjected to controlled denaturing of the DNA. This denaturing generates single chain DNA sections from the ends of the breakages, which are detected by in situ hybridisation using a total genomic DNA probe labelled with a fluorochrome, visible using a fluorescence microscope. When the level of breakages in the cell DNA is higher, the higher is the quantity of the hybridised probe and the fluorescence observed is higher. The samples processed according to the method described in the present invention, contain single chain DNA, created by the denaturing solution, from the possible ends of the breakage which exist in DNA. Therefore, the intensity of the hybridisation using the total genomic DNA probe, will be in relation to the quantity of breakages present in the sperm nucleus. In this way we have confirmed that the nucleoids without a halo, or with a halo much reduced in size, show an intense labelling with DBD-FISH, which demonstrates the intense fragmentation of its DNA (FIG. 2). The rest of the nucleoids show very low levels of marker with this probe, which correspond to the depth of hybridisation by the chromatin treatment itself.

The invention also contemplates a Kit for the evaluation of the integrity of the chromatin/DNA of animal sperm. This Kit contains a DNA denaturing solution, a lysis solution to extract the nuclear proteins, which is characterised in that the lysis solution does not contain a protein denaturing detergent and essentially does not destroy the tails of the sperm. The preferred DNA denaturing solutions and the preferred lysis solutions are described above.

Optionally, the Kit can also contain the pre-treated support, for example with agarose, as well as a solution for the preparation of a medium with characteristics similar to a suspension which would contain the sample. For example, a low gelling point agarose solution which allows a microgel to be prepared.

The contents and the instructions for use of a Kit according to a variation of the invention is detailed below:

Description of the Contents of the Kit
Pre-treated slides*
Eppendorf tubes containing of low gelling point agarose tube (A)
Tube with 37% HCl, tube (B)
Tubes with lysis solution, tube C*. Composition: 2.5M NaCl, 0.2M DTT, 0.2M Tris, 1% Triton X-100, pH 7.5
Processing recipients for the denaturing solution and for the lysis solution.
Lancet
Floats for the Eppendorf tubes
*Preparation as referred to earlier in the description.
Material and Equipment Required
Clear field or fluorescence microscope (immersion objective recommended)
Refrigerator at 4° C.
Incubation bath at 37° C.
Plastic gloves
Glass cover slips (18×18 mm, 22×22 mm or 24×60 mm)
Micropipettes
4 horizontal containers for incubation
Distilled water
70%, 90%, 100% Ethanol
Instructions for Use
Preparation of a Sample for Slides
1) Take a flask C to place the lysis solution at ambient temperature (22° C.)
2) Dilute the semen sample in culture media or PBS, to a concentration of 5-10 million per milliliter. Fresh or samples directly frozen in liquid nitrogen can be used.
Preparation of the Agarose Microgel
3) Gently tap an Eppendorf tube containing low gelling point agarose (Tube A), in the vertical position, to deposit the agarose at the bottom of the tube.
4) Add 140 microliters of distilled water, avoiding the formation of bubbles, and resuspend.
5) Introduce Tube A into the float, leaving it at the level of the cap, and let it float 5 minutes in water at 90-100° C., until the agarose is dissolved. The melting of the agarose can alternatively be carried out in a microwave oven.
6) Transfer the Tube A with the float, to a 37° C. thermostatic bath, and leave for 5 minutes to reach temperature.
7) Add 60 microliters of the semen sample to the contents of Tube A and resuspend.
8) Place a pre-treated slide on a cold surface, at 4° C. (for example, a metal or glass sheet).
9) Once the slides have cooled, deposit the cell suspension of Tube A and place a glass cover slip, avoiding forming air bubbles. It is recommended to deposit a drop of 11, 17 and 50 microliters, for a cover slip of 18×18 mm, 22×22 mm or 24×60 mm, respectively.
10) Place the cold sheet with the slides in the refrigerator and leave the sample to gel for 5 minutes.

Processing the Samples
11) Prepare the denaturing solution. For this, add 80 microliters of the contents of Tube B in 10 microliters of distilled water, mix and place in the green box.
12) Remove the cover slips, sliding them gently, and immediately place the slide, horizontally, in the denaturing solution and leave to incubate for 7 minutes, at ambient temperature (22° C.).
13) Lift the slides with the aid of the lancet, using gloves. Hold them horizontally, and place them horizontally in the white recipient containing 10 ml of lysis solution (Tube C brought to temperature). Incubate for 25 minutes.
14) Lift the slides and place them horizontally in a container holding abundant distilled water to wash off the lysis solution. Leave for 5 minutes.
15) Place the slides, horizontally, into a container with 70% ethanol (2 minutes), then in 90% ethanol (2 minutes), and finally in 100% ethanol (2 minutes).
16) Leave to dry in air. Once the processed slides are dry they can be stored in filing cabinets, at ambient (room) temperature for months.

Staining of the Samples
Staining to observe under a clear field microscope:
   Mix the Wright's solution with phosphate buffer (1:1), and deposit a layer of stain, horizontally, that will cover the dry microgel. Leave to stain for 5-10 minutes, blowing over it occasionally. Decant, wash gently with running water and leave to dry. If the stain is excessive, it can be destained in ethanol, dried and stained again. If the stain is weak, particularly in the halos, it can be stained again with more Wright's solution.
   Another possibility is incubation for 5 minutes, vertically, in a Coplin jar with Hemacolor 2 solution (Merck 1.11956), leave to drain vertically for 10 seconds and then incubate in another Coplin jar, vertically, with Hemacolor 3 solution (Merck 1.11957), for 5 minutes. Finally, wash gently in distilled water and leave to dry. If a permanent preparation is desired, this can be mounted in Entallan.

Staining for observing under a fluorescence microscope:
Depending on the variability of fluorescence filters, the samples can be stained with fluorochromes specific for DNA of the DAPI type, Hoechst 33258, Ethidium Bromide, Propidium Iodide, etc., in an antifading medium (for example Vectashield, Vector, ref: H-1000).

Safety and the Environment
Avoid inhalation and contact with the supplied solutions.
Solutions B and C contain hydrochloric acid, dithiothreitol and Triton X-100.
Consult the specifications supplied by the manufacturers.
Do not dispose of the products used into the environment.
Follow the guidelines of the Centre for the storage and disposing of toxic products.
The biological samples must be handled as potentially infectious.

Storage and Stability
Store at ambient (room) temperature, except solution C which must be stored at 4° C. Expiry: the reagents and materials are stable for a minimum period of 6 months. It is recommended that solutions B and C are kept in the vertical position and well sealed.

The present invention has different fields where its application is relevant. Its use in human applications is obvious. For example, in samples from infertile individuals whose seminogram parameters are normal, in couples with repeated miscarriages, in samples used for assisted reproduction, in samples that are going to be frozen (cryo-preservation) for their future use in assisted reproduction techniques due to extirpation of the testicle. Also in patients subjected to chemotherapy and/or radiotherapy due to oncological diseases, and before carrying out a vasectomy.

The study carried out with the procedure and the Kit of the invention can improve the selection criteria of sperm donor candidates, as well as complementing the periodic evaluation of the samples from donors, in sperm banks. It is also possible to analyse the effect of advanced age on the quality of semen and fertility. Its application is interesting for the evaluation of patients with diseases which could affect the integrity of the sperm: fever, infections, variocele, stress, exposure to genotoxic agents at work or accidental (pesticides, radiation, environmental oestrogens, etc.), hormone treatments, or repeated exposure to increased heat (professions associated with hot ovens, ceramic, glass, or drivers of vehicles). These individuals can also be evaluated periodically. Lastly, the invention is useful in basic and clinical research.

Similarly, the invention is also of use in, veterinary laboratories. It is possible to study the level of DNA fragmentation in different animal species, for example breeding males, in stored samples, in disease processes, in the males of species in danger of extinction and in the evaluation of damage caused by toxic agents.

EXAMPLES

The invention will be described on the basis of some examples that will illustrate in more detail some of the previously described characteristics.

Example 1

In a sample of fresh semen, the described methodology is applied to produce chromatin dispersion halos. For this, the sample diluted to a concentration of 10 million per milliliter, in PBS, was mixed with 1% liquid low gelling point agarose, to obtain a final concentration of 0.7% of the latter. After the microgel has gelled over the slide, the sample was incubated at 22° C. for 8 minutes in the denaturing solution composed of 0.08M HCl, and then in the lysis solution consisting of 2.5M NaCl, 0.2M DTT, 0.2M Tris, 1% Triton X-100, pH 7.5, for 25 minutes, at 22° C. The slides were washed in distilled water for 5 minutes, they were dehydrated in ethanol baths, and they were dried in air. Then, sequentially and on the same cells, DBD-FISH (DNA Breakage Detection-Fluorescence In Situ Hybridization; Fernandez et al., 1998; 2000; 2002; Fernandez and Gosalvez, 2002), was then carried out using a total genomic DNA probe. This procedure enables the detection and quantifying of breakages of the DNA in cell nuclei immersed in agarose microgel, deproteinised and subjected to a controlled denaturing of the DNA. This denaturing produces sections of single chain DNA from the ends of the breakage, which are detected by means of in situ hybridisation using a total genomic DNA probe labelled with a fluorochrome which emits red fluorescence (Cy3). The higher the number of breakages in the cell DNA, the higher is the quality of the single chain DNA produced by the denaturing solution, the higher is the quantity of the hybridised probe and the higher is the red fluorescence obtained. The samples processed according to the procedure of the present invention contain single chain DNA, produced by the denaturing solution, from the possible ends of the breakages that the DNA has. Therefore, the intensity of the hybridisation using the total genomic DNA probe, will be in relation to the amount of breakages present in the nucleus of the sperm.

250 cells obtained at random were counted. The DAPI stained images of the chromatin dispersion halos, were captured using a refrigerated CCD camera using two filters to visualise the dispersion halos, visible in blue, and the hybridisation signal, visible in red, simultaneously. The final aim was to establish a correlation between the size of the chromatin dispersion halos and the level of marker of the DNA breakages. The results demonstrated an inverse correlation between the relative area of the chromatin dispersion halos and the intensity of the marker of DNA breakages using DBD-FISH (Table 1).

TABLE 1

|  | Halo area/total | Total MD |
|---|---|---|
| LARGE HALO | | |
| Mean | 0.85 | 13.07 |
| Standard deviation | 0.05 | 7.35 |
| Count | 154 | 154 |
| MEDIUM HALO | | |
| Mean | 0.73 | 24.85 |
| Standard deviation | 0.07 | 12.52 |
| Count | 38 | 38 |
| SMALL HALO | | |
| Mean | 0.48 | 180.28 |
| Standard deviation | 0.14 | 117.82 |
| Count | 22 | 22 |
| WITHOUT HALO | | |
| Mean | — | 407.34 |
| Standard deviation | — | 252.69 |
| Count | 29 | 29 |
| DEGRADED | | |
| Mean | — | 101 |
| Standard deviation | — | 86 |
| Count | 7 | 7 |

Note that as the relative area of the halo decreases, an increase in the total mean density (MD) of the hybridisation is produced.

As a result, the simple determination of the size of the chromatin dispersion halos, obtained using our procedure, offers a simple and direct estimation of the integrity of the chromatin/DNA of human sperm.

Example 2

A Complementary Method for the Evaluation of Sperm Donors Used in Assisted Reproduction Techniques.

In an assisted reproduction clinic, 10 semen donor samples were taken. As a complement to the routine spermogram, the level of DNA fragmentation was determined in these samples. 500 cells per individual were counted. In this case the results were obtained by applying the chromatin dispersion halos test of the invention. The samples were included into the agarose microgel, were incubated in the acid and lysis solutions, were washed, dehydrated and left to dry, as described in Example 1. The staining, in this case, was not done with DAPI but with the Wright stain, for clear field microscopy. For this the Wright's solution was mixed with phosphate buffer (1:1), and a layer of stain was placed, horizontally, covering the dry microgel. It was stained for 5-10 minutes, blowing over it occasionally. After a wash in running water, it was left to dry and the nucleoids were visualised. The results are shown in Table 2. The mean fragmentation level in this group was less then 20% in all cases (15.4±3.1).

TABLE 2

| Sample No. | % Large halo Cells | % Medium halo Cells | % Small halo Cells | % Cells without halo | % Degraded cells | % Fragmented cells |
|---|---|---|---|---|---|---|
| n1 | 76.2 | 7.4 | 10.2 | 5.0 | 1.2 | 16.4 |
| n2 | 74.4 | 7.0 | 11.2 | 7.4 | — | 18.6 |
| n3 | 72.6 | 16.4 | 6.2 | 4.8 | — | 11.0 |
| n4 | 78.6 | 6.0 | 7.4 | 6.6 | 1.4 | 15.4 |
| n5 | 81.6 | 5.8 | 7.0 | 5.4 | 0.2 | 12.6 |
| n6 | 69.4 | 11.0 | 12.6 | 6.0 | 1.0 | 19.6 |
| n7 | 73.2 | 7.2 | 9.6 | 8.8 | 1.2 | 19.6 |
| n8 | 80.2 | 5.4 | 8.4 | 5.0 | 1.0 | 14.4 |
| n9 | 85.2 | 2.6 | 5.0 | 6.8 | 0.4 | 12.2 |
| n10 | 79.8 | 5.6 | 6.8 | 7.0 | 0.8 | 14.6 |

Distribution of the percentages of the size categories of the halos obtained in 10 semen donors. The percentage of sperm with fragmented DNA consisted of the sum of the sperm categories with a small halo, without halo and without halos-degraded.

Example 3

Clinical Evaluation of Infertile Patients

In an assisted reproduction clinic, 17 samples were taken from sperm donors. As a complement to the routine spermogram, the level of DNA fragmentation was determined in these samples. 500 cells per individual were counted. As in the previous example, the results were obtained by applying the chromatin dispersion halos test of the invention. The results are shown in Table 3. The mean level of fragmentation in this group was over 20% in all cases (49.9±20.7).

TABLE 3

| Sample No. | % Large halo Cells | % Medium halo Cells | % Small halo Cells | % Cells without halo | % Degraded cells | % Fragmented cells |
|---|---|---|---|---|---|---|
| p1 | 47.0 | 12.0 | 16.2 | 22.4 | 2.4 | 41.0 |
| p2 | 38.4 | 3.2 | 15.2 | 42.2 | 1.0 | 58.4 |
| p3 | 39.6 | 1.6 | 13.2 | 44.6 | 1.0 | 58.8 |
| p4 | 53.4 | 10.6 | 11.0 | 17.6 | 7.4 | 36.0 |
| p5 | 42.4 | 5.2 | 15.2 | 35.8 | 1.4 | 52.4 |
| p6 | 50.0 | 5.8 | 10.0 | 32.9 | 1.2 | 44.2 |
| p7 | 39.0 | 11.2 | 22.6 | 21.2 | 6.0 | 49.8 |
| p8 | 60.6 | 4.8 | 9.4 | 22.8 | 2.4 | 34.6 |
| p9 | 69.4 | 3.2 | 7.4 | 19.0 | 1.0 | 27.4 |
| p10 | 60.6 | 4.4 | 10.4 | 24.0 | 0.6 | 35.0 |
| p11 | 11.3 | 3.0 | 6.0 | 75.8 | 4.0 | 85.8 |
| p12 | 65.6 | 4.2 | 2.4 | 24.4 | 3.4 | 30.2 |
| p13 | 16.7 | 11.9 | 24.3 | 46.8 | 0.3 | 71.4 |
| p14 | 8.4 | 4.4 | 18.6 | 67.0 | 1.6 | 87.2 |
| p15 | 64.7 | 8.2 | 11.2 | 13.7 | 2.2 | 27.1 |
| p16 | 14.6 | 5.0 | 10.6 | 63.4 | 6.4 | 80.4 |
| p17 | 65.8 | 5.8 | 9.4 | 17.4 | 1.6 | 28.4 |

Distribution of the percentages of the size categories of the halos obtained in 17 patients. The percentage of sperm with fragmented DNA consisted of the sum of the sperm categories with a small halo, without halo and without halos-degraded.

Example 4

The invention was used to evaluate the toxicological damages that affects human sperm. Damage by exogenous and endogenous agents.

As an illustrative example a study is presented which analysed the DNA damage induced by a nitric oxide (NO) donor chemical agent. For this, aliquots of 50 microliters of a totally fresh semen sample of a normal individual, was incubated for 1 hour, at ambient (room) temperature, with different doses of sodium nitroprussate (SNP). The treated samples were then centrifuged gently, discarding the supernatant, to wash the SNP. After resuspending in PBS, the samples were processed according to the method described in the present invention.

The results are presented in Table 4. It is observed that as concentration of the NO donor was increased, the percentage of sperm with damaged chromatin/DNA increased.

TABLE 4

| Concentration of SNP (microM) | % Large halo Cells | % Medium halo Cells | % Small halo Cells | % Cells without halo | % Degraded cells | % Fragmented cells |
| --- | --- | --- | --- | --- | --- | --- |
| 0.0 | 61.8 | 14.1 | 12.0 | 12.1 | 0.0 | 24.1 |
| 62.5 | 38.0 | 23.2 | 19.6 | 19.2 | 0.0 | 38.8 |
| 125 | 21.8 | 24.2 | 32.6 | 23.1 | 0.0 | 55.7 |
| 250 | 14.9 | 19.0 | 40.3 | 30.1 | 0.0 | 70.4 |
| 500 | 3.8 | 22.5 | 39.6 | 34.1 | 0.0 | 73.7 |

Distribution of the percentages of the size categories of the halos obtained in a sample of semen treated with different concentrations of a nitric oxide (NO) donor agent, with capacity to produce damage in DNA. The percentage of sperm with fragmented DNA consisted of the sum of the sperm categories with a small halo, without halo and without halos-degraded.

Example 5

Reproducibility of the Assay Using Frozen Semen Samples.

Two factors which could affect the quality of the samples were studied, such as freezing and dilution, using the methodology by analysis of the degree of chromatin halo dispersion. For this 4 fresh samples from different donors, and aliquots frozen in liquid nitrogen were analysed. The analysis of the samples was carried out by direct visual count of the different types of nucleoids (500 cells), on two different slides and a minimum of two times, per sample and experimental point.

Reproducibility of the counts. The intra-class coefficient of correlation (R) was calculated for the different measurements that were carried out on each slide. The results of the indices for each cell type and calculations with the average of two counts varied between values of 0.78 and 0.92, and given that the R values vary between 0 and 1, it shows that a high reproducibility was obtained (Table 5).

TABLE 5

| | Mean | 95% Confidence Limits |
| --- | --- | --- |
| % Difference large halo cells | −0.78 | (−1.98; 0.42) |
| % Difference medium halo cells | 0.56 | (−0.17; 1.29) |
| % Difference small halo cells | 0.36 | (−0.48; 1.20) |
| % Difference cells without halo | −0.19 | (−0.88; 0.50) |
| % Difference cells without halo and degraded | 0.04 | (−0.35; 0.43) |
| % Difference cells with fragmented DNA | 0.21 | (−0.67; 1.09) |

Freezing. The results obtained are compared using an analysis of variance of two factors (preservation method and sample). It was shown that there were no significant differences ($P>0.05$) in the level of fragmentation of the samples processed fresh and frozen in liquid nitrogen. Neither did the time frozen appear to affect the proportion of sperm with fragmented DNA (Table 6).

TABLE 6

| Sample | State of Sample | Mean | Standard deviation |
| --- | --- | --- | --- |
| 1 | S. Fresh | 19.58 | 0.22 |
|   | S. Frozen | 20.20 | 1.48 |
| 2 | S. Fresh | 13.38 | 1.87 |
|   | S. Frozen | 13.39 | 1.86 |

TABLE 6-continued

| Sample | State of Sample | Mean | Standard deviation |
| --- | --- | --- | --- |
| 3 | S. Fresh | 12.75 | 3.04 |
|   | S. Frozen | 11.53 | 1.92 |
| 4 | S. Fresh | 22.13 | 0.74 |
|   | S. Frozen | 21.56 | 2.68 |

In conclusion, the reproducibility of the results obtained after direct visual analysis is demonstrated.

Example 6

Analysis of the Integrity of the Chromatin/DNA of Human Sperm Using the Variation of the Incubation Order of the Denaturing and Lysis Solutions:

In this variation, after placing the sperm in the agarose microgels, they are incubated, in a first step, in the lysis solution described in the Kit, for 25 minutes, at 22° C. The slides are then submerged in the denaturing solution composed of 0.88 HCl, for 8 minutes, at 22° C. Finally, after the distilled water wash, the slides are dehydrated and stained with the Wright's solution, and observed using a clear field microscope.

Using this technical variation, the sperm with fragmented DNA behave in a different way. In this case, they disperse chromatin/DNA fragments, giving rise to larger sized halos.

Example 7

Results of the Application of the Methodology on Sperm Samples of Different Animals.

Figure 4:
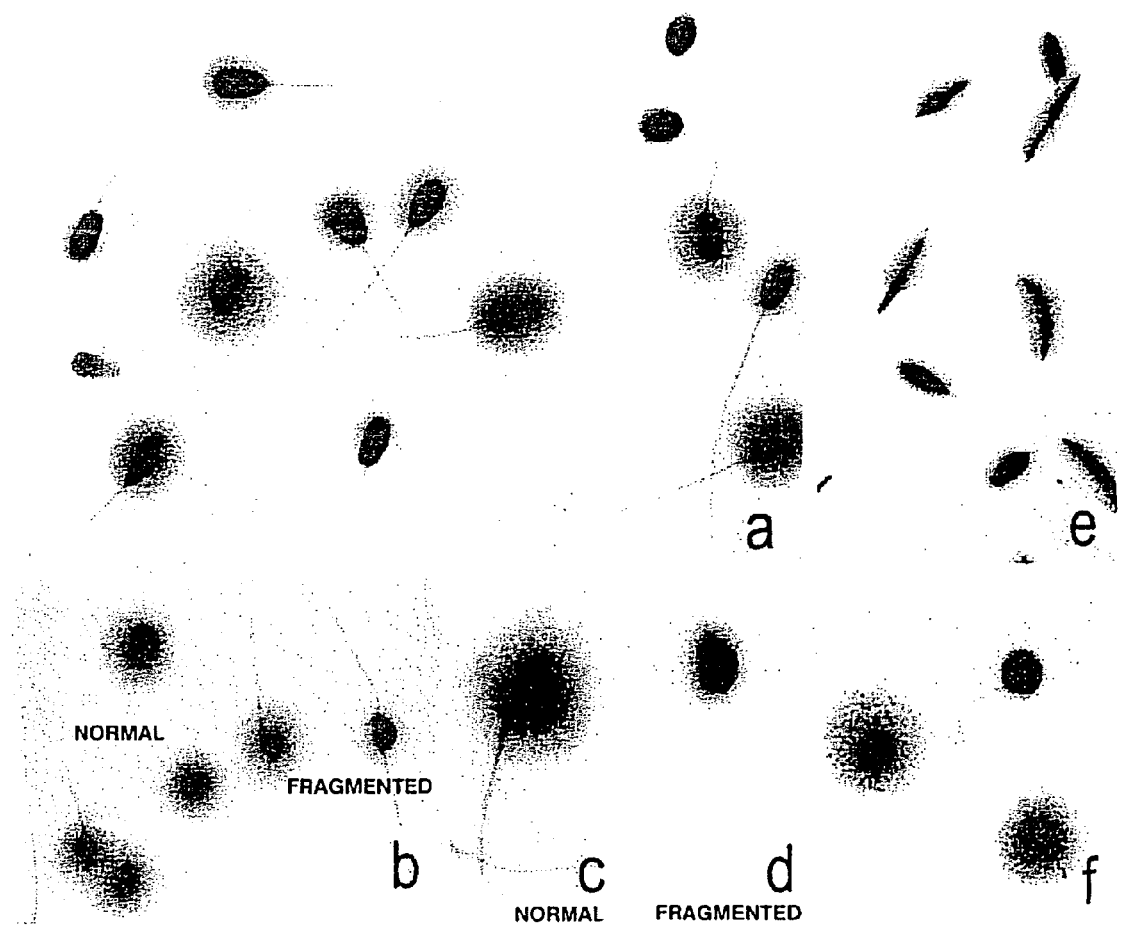
FIG. 4. Application of the method of the invention to the sperm samples of the following species: mouse (*Mus musculus*), bull (*Bos taurus*), turbot (*Scophthalmus maximus*) and earth worm (*Lombricus terrestris*). 4a, corresponds to a bull; 4b, c, d correspond to mouse; 4e corresponds to earthworm; 4f corresponds to the turbot.

With the objective of evaluating the universal character of the methodology that is proposed, male individuals of different species were selected to carry out a study of the levels of DNA fragmentation in the sperm and the parallel visualisation of their tail as a distinctive cellular element. Samples of sperm were taken from the following species: mouse (*Mus musculus*), bull (*Bos taurus*), turbot (*Scophthalmus maximus*) and earth worm (*Lombricus terrestris*). In all the species, the application of the technique produced chromatin dispersion halos and their tails could be recognised, including those which had normal DNA as well as those that had it fragmented (FIG. 4). The form of the sperm and the type of halo produced, is characteristic of each species (4a corresponds to the bull; 4b, c, d correspond to the mouse; 4e corresponds to the earth worm; 4f corresponds to the turbot. The morphology of the sperm, whether it contained fragmented DNA or not, is different between species and in turn different to that found in humans. In all cases, the chromatin dispersion is parallel and comparable to that found in the case of human sperm samples. That is to say, chromatin dispersion halos of a different size are produced and the tail of the sperm can be visualised.

The morphology and size of the halos of the different species and the results obtained were the following:

In the case of the bull, independent samples were analysed using 5 different observers. In this case, differences were found in the percentage of sperm nuclei with fragmented DNA by each individual, but no differences were observed between the percentages obtained between each observer (Table 7).

TABLE 7

| | TOTAL | | | | | |
|---|---|---|---|---|---|---|
| | % Large | % Medium | % Small | % Without halo | % Degraded | % Fragmented |
| Ob1-500 | 75.8 | 9.8 | 7.2 | 7.2 | 0 | 14.4 |
| Ob2-500 | 77 | 7.2 | 12 | 3.6 | 0.2 | 15.8 |
| Ob3-500 | 77 | 8 | 9.8 | 5 | 0.2 | 15 |
| Ob4-500 | 72.8 | 11.4 | 8.8 | 7 | 0 | 15.8 |
| Ob5-500 | 73 | 11.2 | 8.2 | 7.6 | 0 | 15.8 |
| 500 | 75.1 | 9.4 | 9.1 | 5.9 | 0.1 | 15.3 |
| Ob1-500 | 80.6 | 10 | 6.2 | 3.2 | 0 | 9.4 |
| Ob3-500 | 82.2 | 8 | 6 | 3.8 | 0 | 9.8 |
| Ob4-500 | 82.4 | 8.4 | 6.2 | 3 | 0 | 9.2 |
| 500 | 81.7 | 8.8 | 6.1 | 3.3 | — | 9.5 |
| Ob1-500 | 71.2 | 6.2 | 10.8 | 11.4 | 0.4 | 22.6 |
| Ob2-500 | 70.8 | 4.6 | 14 | 10.6 | 0 | 24.6 |
| Ob3-500 | 75 | 5.6 | 12 | 7.2 | 0.2 | 19.4 |
| Ob5-500 | 72.2 | 6.8 | 14.2 | 6.4 | 0.4 | 21 |
| 500 | 72.3 | 5.7 | 12.7 | 8.6 | 0.3 | 21.8 |
| Ob2-500 | 85.2 | 8.4 | 3.8 | 2.6 | 0 | 6.4 |
| Ob3-500 | 84.4 | 10 | 3.2 | 2.4 | 0 | 5.6 |
| Ob4-500 | 80.8 | 12.8 | 4 | 2.4 | 0 | 6.4 |
| 500 | 83.4 | 10.2 | 3.7 | 2.5 | 0 | 6.1 |

In the case of the mouse, two different strains were used, one normal (M1-32NNC) and another consanguineous (M2-32BC). The percentages obtained for the different types of halos show clear differences between a normal (7.1) and a consanguineous (25.1) strain (Table 8).

TABLE 8

| | TOTAL | | | | | |
|---|---|---|---|---|---|---|
| | % Large | % Medium | % Small | % Without halo | % Degraded | % Fragmented |
| M2-32BC | 63 | 11.5 | 18.1 | 6.9 | 0.1 | 25.1 |
| M1-32NNC | 86.2 | 6.5 | 4.6 | 2.5 | 0.2 | 7.1 |

In the specific case of the turbot, sperm that had a large chromatin dispersion halo and a small core could be distinguished against those that had a small dispersion halo and a large core and finally, others without a dispersion halo. The results are displayed in Table 9.

TABLE 9

| % Large Halo/ Small Core | % Small Halo/ Large Core | % Only Head Without Halo |
|---|---|---|
| 94 | 5.6 | 0.4 |
| 92.8 | 7 | 0.2 |
| 95.6 | 4 | 0.4 |
| 94.1 | 5.4 | 0.3 |
| 72.2 | 25.2 | 2.6 |
| 71.6 | 25.4 | 3 |
| 77 | 20.2 | 2.8 |
| 73.6 | 23.5 | 2.8 |
| 75.2 | 18.4 | 6.4 |
| 71.2 | 22 | 6.8 |
| 78 | 15 | 7 |
| 74.7 | 18.2 | 6.7 |

In the case of the earth worm, a dynamic generation of halos similar that described in the previous cases is produced, and in this case the head of the sperm and its tail can also be distinguished perfectly. The estimated percentage of sperm that contain fragmented DNA in 2 individuals studied (one young and one mature) was 15% and 22%, respectively. In this case, sperm heads appear with partial halo formation, the significance of which is currently in the investigation phase (see FIG. 4e).

Example 8

Visualisation of the Same Cytological Preparation of Chromatin Dispersion Halos, Sperm Tails and Leucocytes. Evaluation of the Effect of Leucocytospermia on the Integrity of DNA in Samples of Sperm.

Leucocytospermia is an undesired invasive process which leads to the abnormal increase of leucocytes in samples of seminal fluid (>5×106/ml). Leucocytospermia has been detected in between 10% and 20% of infertile males. 10 It seems that the neutrophils as well as the macrophages present in semen can generate ROS (Reactive Oxygen Species) which bring about oxidative stress, and results in damage of the DNA in the sperm (Omu et al., 1999; Erenpreiss et al., 2002; Henkes et al., 2003). In fact, leucocytospermia has been associated with different abnormalities of the classic parameters used in the analysis of the 15 quality of sperm. For example, while the incidence of abnormal sperm occurs in only 47% of the samples of individuals without leucocytospermia, the percentage increases to 88% when this leucocytospermia is present See website of the Cleveland Clinic.

Figure 5:
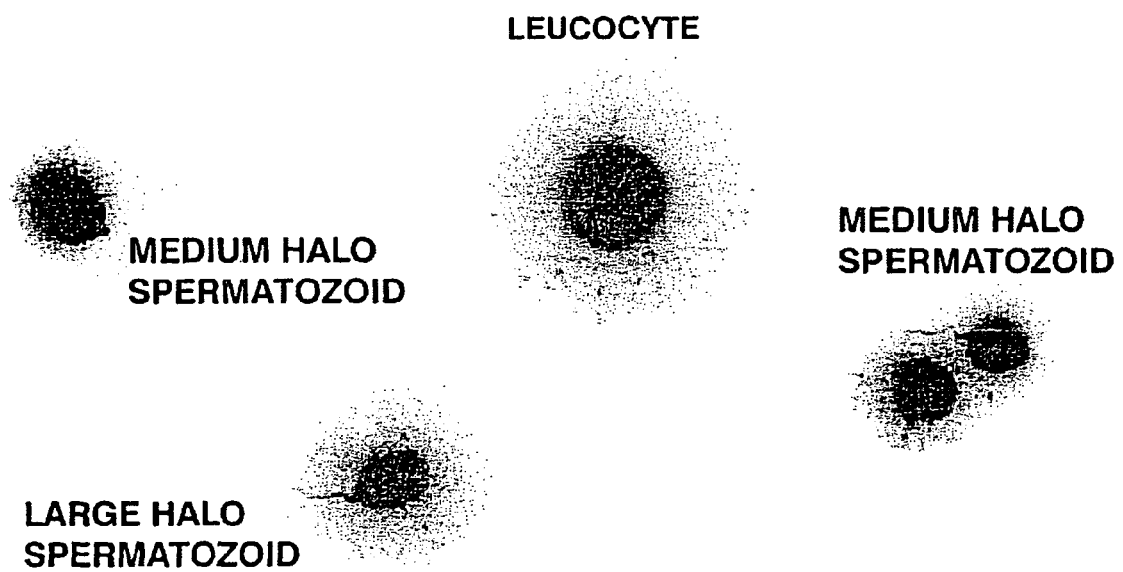
FIG. 5. Sample from a patient with the presence of high levels of leucocytospermia. The absence of a tail in the leucocytes is noted, which allows them to be differentiated from the rest of the cell types.

In a sample of 5 patients, with high levels of leucocytospermia of different aetiology (prostatitis and infections due to chlamydomonas and bacterial agents), the response to the technique was studied to differentiate, unequivocally, the percentage of leucocytes present in the semen samples and the levels of DNA fragmentation in the sperm of the same samples. The difference, between both cell types, when the samples are subjected to the same treatment, is clear, given that the sperm with fragmented DNA as well as those which do not have it, show the tail which characterises them. The absence of a tail in the leucocytes enables us to differentiate them from the rest of the cell types (FIG. 5).

In this way, a direct correlation can be established between the number of leucocytes per sample and the levels of DNA fragmentation in the sperm, Table 10 shows the level of leucocytes in semen samples of 5 patients affected by leucocytospermia of different aetiology and the percentage of sperm with normal DNA (large and medium; L/M) and fragmented (small halo and without halo (S/WH).

TABLE 10

|          | % Leucocytes | % L/M halo cells | % P/WH halo cells |
|----------|--------------|------------------|-------------------|
| Sample 1 | 6.1          | 73.9             | 20                |
| Sample 2 | 15.5         | 55.3             | 29.2              |
| Sample 3 | 17           | 48.2             | 34.8              |
| Sample 4 | 22           | 31.7             | 46.3              |
| Sample 5 | 25.6         | 30.5             | 43.9              |

REFERENCES

Aitken R J, Gordon E, Harkiss D (1998) Relative impact of oxidative stress on the 15 functional competence and genomic integrity of human spermatozoa. Biol. Reprod. 59: 1037-1046

De Jonge C (2002) The clinical value of sperm nuclear DNA assessment Hum. Fertil. 5:51-53

Erenpreiss J, Hlevicka S, Zalkalns J and Erenpreisa J J (2002) Effect of Leukocytospermia on Sperm DNA Integrity: A Negative Effect on Abnormal Semen Samples. Journal of Andrology 23: 5.

Evenson D P, Darzynkiewicz Z, and Melamed, M R (1980) Relation of mammalian sperm heterogeneity to fertility. Science 210:1131-1133

Evenson D P and Jost L K (1994) Sperm chromatin structure assay: DNA denaturability. In: Darzynkiewicz Z, Robinson J P, Crissman H A. eds. Methods in Cell Biology Vol 42. Flow Cytometry 2nd ed. Orlando. Fla: Academic Press 42:159-176)

Evenson D P, Jost L K, Corzett M, Balhorn R (2000) Characteristics of human sperm chromatin structure following an episode of influenza and high fever: a case study. J. Androl. 21: 739-746

Evenson D P, Jost L K, Marshall D, Zinaman M J, Clegg E, Purvis K, de Angelis P, Claussen O P (1999) Utility of the sperm chromatin structure assay as a diagnostic and prognostic tool in the human fertility clinic. Hum. Reprod. 14: 1039-1049.

Evenson D P, Larson N J, Jost L K (2002) Sperm Chromatin Structure Assay: its clinical use for detecting sperm DNA fragmentation in male infertility and comparisons with other techniques. J. Androl 23:25-43

Fernández J L, Goyanes V J, Ramiro J, Gosálvez J (1998) Application of FISH for in situ detection and quantification of DNA breakage. Cytogenet. Cell Genet. 82:251-256

Fernández J L, Vázquez-Gundín F, Delgado A, Goyanes V J, Ramiro-Díaz J, de la Torre J, Gosálvez J (2000) DNA breakage detection (DBD-FISH) in human spermatozoa: technical variants evidence different structural features. Mutat. Res. 453:77-82

Fernández J L, Gosálvez J (2002) Application of FISH to detect DNA damage: DNA breakage Detection-FISH (DBD-FISH). Methods Mol. Biol. 203:203-216.

Fernández J L, Goyanes Y, Gosalvez J (2002) DNA Breakage Detection-FISH (DBD-FISH) In: Rautenstrauss B, Liehr T. eds. FISH technology—Springer lab manual. Heideberg: Springer-Verlag; 282-290.

Fernández J L, Muriel L, Rivero M T, Goyanes Y, Vázquez R, Alvarez J G (2003) The sperm chromatin dispersion test: a simple method for the determination of sperm DNA fragmentation. J. Androl. 24: 59-66

Henkel R, Maass G, Hajimohammad M, Menkveld R, Stall T, Villegas J. Sanchez R, Kruger T F, Schill W B. (2003) Urogenital inflammation: changes of leucocytes and ROS. Andrologia. 35:309-13.

Larson K L. DeJonge C, Barnes A, Jost L, and Evenson D P (2000) Relationship between assisted reproductive techniques (ART) outcome and status of chromatin integrity as measured by the Sperm Chromatin Structure Assay (SCSA). Hum Reprod. 15:1717-1722

Gorczyca W, Gong J, Darzynkiewicz Z (1993) Detection of DNA strand breaks in individual apoptotic cells by the in situ terminal deoxynucleotidyl transferase and nick translation assays. Cancer Res. 53:945-951.

Hughes C M, Lewis S E, McKelvey-Martin V J, Thompson W (1996) A comparison of baseline and induced DNA damage in human spermatozoa from fertile and infertile men using a modified comet assay. Mol Hum Reprod 2:613-619.

Omu A E, Al-Qattan F, Al-Abdul-Hadi F M, Fatinikun M T, Fernandes S. (1999) Seminal immune response in infertile men with leukocytospermia: effect on antioxidant activity. Eur J Obstet Gynecol Reprod Biol 86:195-202 (1999)

Sailer B L, Jost L K, Evenson D P (1995) Mammalian sperm DNA susceptibility to in situ denaturation associated with the presence of DNA strand breaks as measured by the deoxynucleotidyl transferase assay. J Androl. 16:80-87.

Sumner A T (1990) Chromosome banding. Unwin Hyman. London.

World Health Organization (1999) WHO laboratory manual for the examination of the human semen and semen-cervical mucus interaction. Fourth Edition. Cambridge University Press, Cambridge, UK.

The invention claimed is:

1. A method to evaluate the integrity of chromatin/DNA of sperm cells of an animal comprising the following steps in sequence:
    a) treating a sample containing the sperm, with a solution of DNA denaturing solution,
    b) a single treatment step of treating the sample in the solution obtained in step a) with a single lysis solution to extract nuclear proteins of the sperm cells, wherein the DNA denaturing solution and the lysis solution are different and the lysis solution comprises sodium chloride, between 1 and 3M, dithiothreitol (DTT) between 0.001 and 2M 2-amino-2-(hydroxymethyl)-1,3-propanediol (Tris) between 0.001 and 2M and toctylphenoxyolyethanol (Triton X-100) between 0.1% and 3%, and
    c) evaluating the integrity of the chromatin/DNA of the sperm cells based on measurement of halo size of the sperm cells.

2. The method according to claim 1, wherein the lysis solution comprises 2.5M sodium chloride, about 0.2M DTT, about 0.2M Tris, about 1% Triton X-100 and is of a pH of about 7.5.

3. The method according to claim 1, wherein the DNA denaturing solution is an acid solution.

4. The method according to claim 3, wherein the DNA denaturing solution comprises an acid selected from hydrochloric, acetic, nitric acid or a mixture thereof.

5. The method according to claim 4 wherein the DNA denaturing solution comprises hydrochloric acid.

6. The method according to claim 1 wherein after steps a) and b) there is a sample staining step.

7. The method according to claim 6 wherein the staining is made with a Wright type solution.

8. The method according to claim 7, wherein the sample containing the sperm is included in a medium similar to a suspension.

9. The method according to claim 7, wherein the sample containing the sperm is included in an agarose microgel.

10. A kit for performing the method of claim 1 which comprises:
   a) a DNA denaturing solution;
   b) a single lysis solution to extract nuclear proteins, wherein the lysis solution does not contain a protein denaturing detergent, said lysis solution comprises sodium chloride between 1M and 3M, dithiothreitol (DTT) between 0.001M and 2M, 2-amino-2(hydroxymethyl)-1,3, propanediol (Tris) between 0.001M and 2M and Triton X-100 between 0.1% and 3%; and
   c) instructions for treating the sperm and evaluating the integrity of the chromatin/DNA of the sperm.

11. The method according to claim 8, wherein the medium is a microgel.

12. The method according to claim 1 wherein the integrity of the chromatin of DNA of the sperm cells is evaluated through direct visual analysis by microscopy or by applying digitalized images analysis software.

* * * * *